United States Patent [19]

Merkel

[11] Patent Number: 4,659,309
[45] Date of Patent: Apr. 21, 1987

[54] ORTHODONTIC BRACKET WITH RHOMBOIDAL PROFILE

[75] Inventor: Daniel A. Merkel, Sheboygan, Wis.

[73] Assignee: American Orthodontics Corporation, Sheboygan, Wis.

[21] Appl. No.: 784,794

[22] Filed: Oct. 4, 1985

Related U.S. Application Data

[63] Continuation-in-part of Ser. No. 727,331, Apr. 25, 1985, abandoned.

[51] Int. Cl.4 .................................................. A61C 7/00
[52] U.S. Cl. ............................................ 433/9; 433/16
[58] Field of Search ........................................ 433/16, 9

[56] References Cited

U.S. PATENT DOCUMENTS

| | | | |
|---|---|---|---|
| 3,477,128 | 11/1969 | Andrews | 433/16 |
| 3,660,900 | 6/1972 | Andrews | 433/16 |
| 4,415,330 | 11/1983 | Daisley et al. | 433/16 |

OTHER PUBLICATIONS

"The Standard Straight-Wire" by A Company Inc. 11436 Sorren to Valley Rd, San Diego, Calif. 92121 May 7, 1973.
The "A" Company Product Catalogue, copyright 1981, p. 54, Cuspid Bracket.
The "A" Company Catalog 1981, p. 5.
The "A" Company Attract Bracket 1986.

*Primary Examiner*—Robert Peshock
*Attorney, Agent, or Firm*—Lloyd L. Zickert

[57] ABSTRACT

An orthodontic bracket for use with an archwire to impart corrective forces to a tooth, including a base portion attachable directly to a tooth, a bonding pad or a band and at least one tie wing extending from the base portion which includes gingival and occlusal tips and an archwire slot opening buccolingually and extending mesiodistally. The buccolingual profile of the bracket is rhomboidal, wherein the backside of the base portion and the front face are parallel and the occlusal and gingival sides are parallel, while an obtuse angle is defined between the outer face of the bracket and one of the occlusal or gingival sides depending upon the tooth on which the bracket is mounted and the torque desired.

12 Claims, 10 Drawing Figures

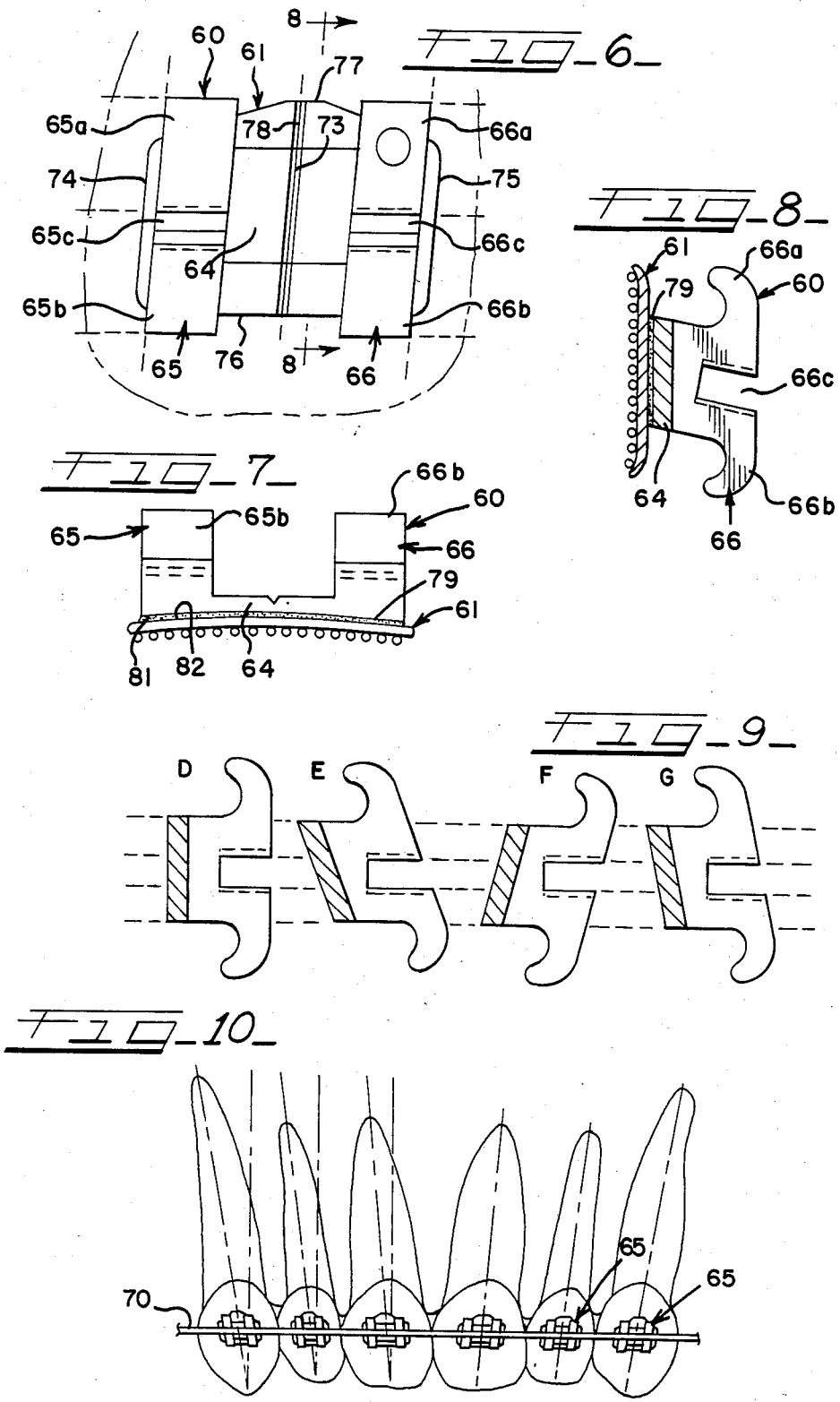

4,659,309

ORTHODONTIC BRACKET WITH RHOMBOIDAL PROFILE

DESCRIPTION

This is a continuation-in-part application of my copending application Ser. No. 727,331, filed Apr. 25, 1985 and now abandoned.

This invention relates in general to an orthodontic bracket for straightening teeth, and more particularly to an edgewise orthodontic bracket having a rhomboidal profile that enhances the compactness of the bracket for greater comfort so that it is less subject to damage in the masticatory process.

BACKGROUND OF THE INVENTION

Heretofore, orthodontic brackets profiled to provide the necessary corrective forces have been objectionable because of excessive labiobuccal projection and only mountable where interference in the masticatory process may be frequently encountered. Particular problems of mounting efficiency for attaining a desired end goal in orthodontic treatment have caused the need for longer treatment times partly because of discomfort to the patient and partly because of failure during wearing by a patient. Problems also have been encountered in the need to particularly dispose an archwire slot at a desired torque and/or angulation which causes weakness in critical areas and sometimes failure during use. Adding mass to these areas likewise increases size.

Prior art brackets either machine torque into the archwire slot or build it into the base, both of which require more mass and/or excessive projection of the wing tips.

SUMMARY OF THE INVENTION

The present invention overcomes the above problems in providing an orthodontic bracket that is more compact in that it is smaller occlusogingivally and smaller labiolingually, thereby making it more compact and easier to wear in the mouth. Further, the present invention builds the torque and/or angulation into the bracket body. As such, the bracket of the present invention promotes the comfort of the patient and is more aesthetically pleasing, thereby inducing a higher level of patient cooperation. The bracket of the invention has a buccolingual profile of rhomboidal configuration wherein the occlusal and gingival sides are parallel and the backside and front face are parallel and an obtuse angle is defined between the front face and one of the occlusal or gingival sides depending upon the tooth for which the bracket is designed. Further, the side walls of the archwire slot are disposed parallel to the occlusal and buccal sides of the bracket. This profile enhances the compactness of the bracket and also allows mounting of the bracket such that it is less likely that crooked teeth will engage the bracket and possibly damage the bracket during masticatory action. Further, the present invention enhances the strength of the bracket by eliminating any possible weak points.

It is therefore an object of the present invention to provide a new and improved orthodontic bracket for use with an archwire to impart corrective forces to a tooth and which has a rhomboidal profile enhancing compactness which promotes patient comfort and aesthetics, and permits positioning on a tooth to decrease the chances of engagement by crooked teeth.

Another object of the present invention is to provide a bracket having a profile that brings both tips of the tie wings to the closest possible proximity to the tooth surface to enhance comfort and aesthetics.

Another object of the present invention is to provide a bracket having a low profile placing the archwire as close as possible to a tooth to enhance the action of archwire forces.

A further object of the present invention is to provide a low profile bracket with a labial profile coacting with the buccolingual profile to facilitate line-up and mounting procedures.

A still further object of the invention is to provide a bracket and pad assembly that facilitates lineup and mounting procedures.

Other objects, features and advantages of the invention will be apparent from the following detailed disclosure, taken in conjunction with the accompanying sheets of drawings, wherein like reference numerals refer to like parts, in which:

BRIEF DESCRIPTION OF THE DRAWINGS

FIG. 6 is a front or labiobuccal view of a twin tie wing bracket of the invention mounted on a pad or base which is also unique;

FIG. 7 is a bottom plan view of the bracket and base assembly shown in FIG. 6;

FIG. 8 is a vertical sectional view taken through the bracket and base assembly of FIG. 6 and also showing a side elevational view of one of the tie wings;

FIG. 9 is a side elevational view of a plurality of brackets of which E, F and G are brackets of the present invention; and FIG. 10 is a layout view of the anterior teeth with brackets of the invention mounted thereon and illustrating the manner in which the archwire slots align and the association of the archwire with the slots.

DESCRIPTION OF THE INVENTION

Figure 1:
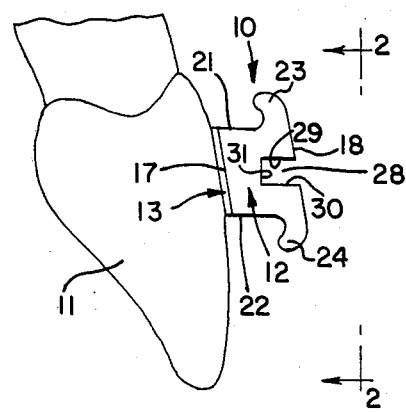
FIG. 1 is a side elevational view or profile view of the bracket of the present invention mounted on an anterior tooth.
Figure 2:
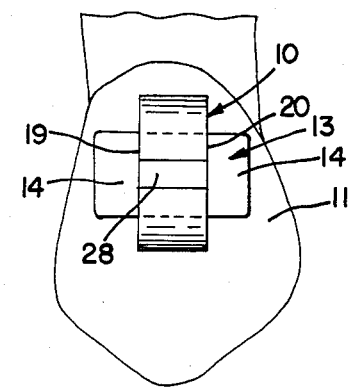
FIG. 2 is a front elevational view of the bracket and tooth of FIG. 1 taken generally along line 2—2 of FIG. 1.
Figure 3:
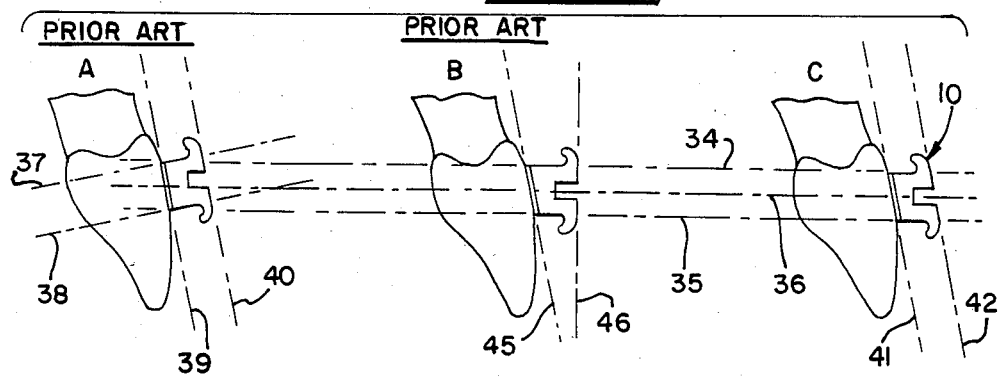
FIG. 3 is a composite view of two prior art brackets mounted on anterior teeth and a view like that of FIG. 1 of the present invention to illustrate the comparison of the present invention with the prior art brackets.
Figure 4:
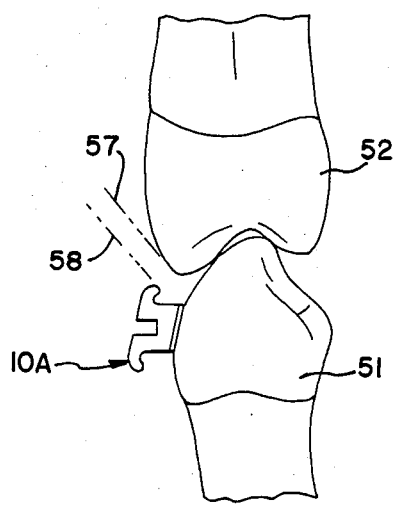
FIG. 4 is a profile view of the bracket of the present invention mounted on a lower bicuspid in occlusion with an upper bicuspid to illustrate the positioning of the bracket of the invention relative to the upper bicuspid.

One form of the bracket of the present invention, illustrated in the drawings in FIGS. 1, 2, 3C and 4, is the single wing type, while another form shown in FIGS. 6 to 10 is the double wing type. The bracket of the invention is especially useful in the well known straight-wire technique. The embodiment shown in FIGS. 1 and 2 is designed for an anterior tooth and particularly a central, while the form shown in FIG. 4 is designed for a lower bicuspid. A positive torque angle is provided in the bracket of FIG. 1, while a negative torque angle is provided in the bracket of FIG. 4, it being appreciated that the torque angle will depend upon the tooth for which the bracket was designed.

The word "profile" as used herein, except when otherwise designated, is usually intended to be understood as a side view along a buccolingual axis of the bracket looking at the mesial or distal side, such as shown in FIG. 1. However, the labial profile will also be described with respect to the embodiment of FIGS. 6 to 10 and then so designated. For simplicity purposes, in terms of bracket style, the form of the bracket illustrated is a standard profile, it being appreciated that other profiles may be provided still within the confines of the present invention. Some of the common styles include the standard profile, low profile, high profile, high gingival wing profile, and beveled occlusal wing profile. These designations would be additional to the rhomboidal profile that is unique to the present invention.

It should be further appreciated that for simplicity purposes the bracket of the invention illustrated in FIG. 2 is a single wing bracket and that a double or triple wing bracket may be provided within the scope of the invention as long as the profile configuration is rhomboidal as hereafter explained. It may be formed of metal by machinery or casting, or molded of plastic or other materials.

Referring now particularly to FIGS. 1 and 2, the bracket of the invention, generally designated by the numeral 10, is illustrated in mounted position on an anterior tooth and particularly a central 11. The bracket includes a tie wing or body 12 integrally formed on a base or pad 13 defining opposed flanges 14. Alternately, although now shown, the tie wing 12 could be separately formed and mounted on a bonding pad or a band, or in any suitable manner otherwise mounted on a tooth surface. For example, the double tie wing type of FIGS. 6 to 10 is shown mounted on a pad or base.

The tie wing includes a backside 17 and a front or buccolabial face 18 parallel to the backside. It is further defined by opposed mesial and distal sides 19 and 20 which are parallel to each other, and gingival and occlusal sides 21 and 22 that are also in parallel arrangement to each other. At the front side of the tie wing, gingival and occlusal tips or hooks 23 and 24 are formed for the purpose of receiving a ligature to secure an archwire on the bracket. Also, at the front face of the tie wing a mesiodistally extending and buccolabial opening archwire slot 28 is formed intermediate the tips having parallel opposed walls 29 and 30 that are also in parallel to the occlusal and distal sides 21 and 22. At the lingual of the walls, a slot base wall 31 extends perpendicular to the opposed walls 29 and 30. While the edges of the bracket are shown to be relatively sharply formed, they will be smoothed or rounded in actual practice. Since the bracket may be made by investment casting, edges and even sides may be rounded. For example, while mesial and distal sides are shown to be flat, they may be easily shaped somewhat rounded when cast, although they will still have a parallel appearance with the opposite sides or surfaces as mirror images.

Because the outer face 18 extends parallel to the backside of the tie wing, the outer face also extends substantially parallel to the surface of the tooth on which the bracket is mounted, thereby disposing both gingival and occlusal tips in the closest possible proximity to the tooth surface, while not interfering with their function of receiving a ligature for securing an archwire to the bracket in the archwire slot.

It can now be seen that the profile of the bracket of the invention as defined by the backside 17, the front face 18, and the gingival and occlusal sides 21 and 22 is rhomboidal, there being an obtuse angle formed between the gingival side 21 and the front face 18. This bracket shown in FIG. 1, being for a central, is designed with a positive torque value, while the bracket of the invention when designed for a lower bicuspid, as shown in FIG. 4, includes a negative torque value. Other torque values are designed into brackets for the other teeth in the usual fashion heretofore well known to bracket manufacturers such as American Orthodontics Corporation of Sheboygan, Wisconsin. Where a negative torque value is designed into the bracket, such as the bracket 10A in FIG. 4, the angle between the front face of the bracket and the gingival side is acute, while that between the front face of the bracket and the occlusal side is obtuse, this being just opposite to that of the bracket 10 design for a central.

A comparison between the bracket of the present invention and two well known prior art brackets is seen by reference to FIG. 3 and demonstrates the advantages of the rhomboidal profile. In this figure brackets have been like mounted on a central tooth so that the relative profiles, position, and relations to the tooth can be readily appreciated. The bracket prior art illustration A is a bracket that has been manufactured and sold for many years by American Orthodontics Corporation of Sheboygan, Wis. The bracket of prior art illustration B has been manufactured and sold for many years by the "A" Company of California, and the bracket of illustration C is the bracket 10 of the present invention. Horizontally extending lines 34 and 35 illustrate that all three brackets are placed on the tooth in the same location where the backside of the bracket is secured to the tooth surface at the same horizontal location.

The archwire slot alignment problem existing with the bracket of prior art illustration A which is solved by the bracket 10 of the present invention in illustration C is illustrated by viewing the intermediate horizontal broken line 36. The parallel lines 37 and 38 associated with illustration A show the reason for a shift in the archwire slot center lines between the bracket of the present invention and this prior art bracket. When the occlusal and gingival sides of the bracket of the present invention are parallel to the central axis of the archwire slot, as shown in illustration C with respect to lines 34, 35 and 36, placement of the bracket slot will be along the same horizontal line from tooth to tooth as accomplished by the bracket in prior art illustration B. Thus, both the prior art bracket B and bracket C of the present invention overcome the slot alignment problem.

The parallel lines 39 and 40, in illustration A representing the backside and front side of the prior art bracket is the same condition that exists with the present invention, as illustrated by lines 41 and 42, where both types extend the same distance from the face of the tooth. However, the upper or gingival tip of the bracket in illustration A is at a lower level than the upper or gingival tip of the bracket of the present invention when the archwire slot is at the same level, as in illustration C. The lines 45 and 46 in illustration B show the wedge or torque in base of this prior art bracket B which requires the non-parallel relation between the front face of the bracket and the backside and also causes the gingival tip to project buccolabially more than the occlusal tip and more than either of the tips in brackets A and C, thereby taking up more room in the mouth and adding to the discomfort of the patient. The upper tip in the bracket of the present invention is shown to be in closer proximity to the tooth surface, thereby illustrating its compactness and adding to the comfort of the patient. Thus, the FIG. 3 comparison shows that the bracket 10 of the present invention is smaller labiolingually and better positioned occlusogingivally than the well known brackets of the prior art. It is also smaller occlusogingivally than bracket A, which needs more mass at critical areas for strength.

Figure 5:
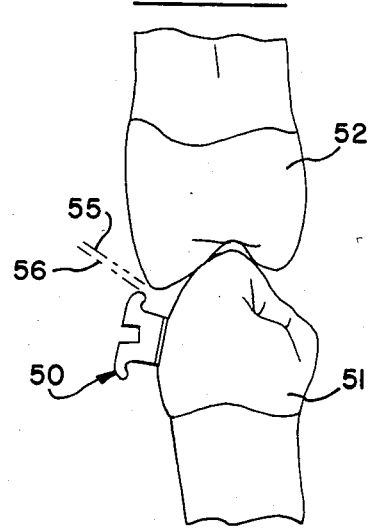
FIG. 5 is a view similar to FIG. 4 except showing a prior art bracket and illustrating the closer positioning of the bracket to the upper tooth.

The rhomboidal configuration of the present bracket is also advantageous for brackets designed for posterior teeth, as illustrated in FIGS. 4 and 5. It will be understood that posterior teeth include the bicuspids and molars, while the anterior teeth include centrals, laterals and cuspids. The prior art bracket 50 shown in FIG. 5 is of the same design as the bracket shown in illustration A of FIG. 3 and is mounted on a lower bicuspid tooth 51 as is the bracket of the present invention with a rhomboidal profile designated 10A in FIG. 4. So as to illustrate the advantages of the present invention over the prior art bracket 50, the lower bicuspid tooth 51 is shown in occlusion with an upper bicuspid tooth 52. The distance between the prior art bracket and the upper bicuspid tooth is measured between the occlusal bracket tip and the tooth by the distance between lines 55 and 56, and is substantially smaller than the distance between the bracket of the present invention and the upper bicuspid tooth as illustrated by the distance between parallel lines 57 and 58. Thus, where masticatory forces are involved and where crooked teeth may engage brackets on the opposite teeth, the present invention serves to space the bracket at the posterior teeth, a distance greater in order to prevent the possibility of damage to the bracket and interference with the planned orthodontic treatment, while at the same time keeping both tips close to the tooth face as opposed to the prior art bracket B. It should be noted that the bracket 10A likewise has a profile with a rhomboidal configuration like the bracket of FIG. 1.

A double wing bracket according to the invention is shown in FIGS. 6 to 10, although it is illustrated with varying torques in FIG. 9. With respect to the bracket shown in FIGS. 6 to 8, it is shown in mounted relation on a unique base or pad developed to complement and coact with the features of the bracket to enhance the mounting of an assembled bracket and pad onto a tooth. The bracket, generally designated by the numeral 60, is shown mounted on the pad or base 61. This bracket includes a base portion 64 and tie wings 65 and 66 extending therefrom. The tie wings respectively include gingival and occlusal tips 65a and 65b for tie wing 65 and tips 66a and 66b for tie wing 66. The tie wings further respectively include labiobuccally opening and mesiodistally extending archwire slots 65c and 66c which are aligned with one another. This bracket, when designed for posterior teeth, has the tie wings extending parallel to each other, as illustrated in FIG. 7.

As seen in FIG. 8, the labiobuccal profile is rhomboidal as in the single wing embodiment shown in FIGS. 1 and 2. Similarly, the side walls of the archwire slots extend parallel to the gingival and occlusal sides of the tie wings. Accordingly, the rhomboidal configuration is embraced likewise in the double wing version of the bracket of the invention, and because of the slot disposition to the tie wings, the torque in the bracket is built into the bracket and may be referred to as diagonal torque. As seen in FIG. 9, where torque is built into the bracket and where it will vary from one bracket to another, as exemplified by brackets E, F and G, which are also shown in relation to a standard-no-torque bracket D, it will be seen that the bracket bases and bracket slots line up with one another, thereby eliminating the need to vary bracket height as is the case with brackets of the type shown in FIG. 3A. Further, the line-up of the components is illustrated in FIG. 10 where bracket pad assemblies are illustrated in mounted relation on centrals, laterals and cuspids and receiving in their archwire slots an archwire 70.

It is also unique to combine with the diagonal torque above referred to the diagonal angulation as is evident particularly in the bracket shown in FIG. 6 and the brackets shown in FIG. 10 wherein the tie wings are angulated to line up with the long axis of the clinical crown of a tooth while still allowing the archwire slot to align horizontally with brackets on adjacent teeth, as shown in FIG. 10. Accordingly, the tie wings 65 and 66 are angulated relative to the vertical as well as relative to the horizontal axis through the bracket. This defines the outer edges of the tie wings as being rhomboidal. In oroder to further assist in mounting of the bracket along the axis of the clinical crown, a groove or scribe line 73 is formed on the outer face of the base portion 64 in parallel alignment with the tie wings and centrally therebetween. Another feature of the invention is to provide the unique base or pad 61 on which the bracket is to be mounted and which also includes an outer rhomboidal configuration.

The pad 61 includes opposed parallel edges 74 and 75 which are arranged in parallel relation to the mesial and distal tie wing edges, a bottom edge 76 in parallel relation to the occlusal edges of the tie wings and spaced inwardly from the tie wing edges, and an upper edge portion 77 extending parallel to the upper or gingival edges of the tie wings, and also lying in a common horizontal plane with the edges. Additionally, the pad 61 includes a groove 78 on its face extending parallel to opposed edges 74 and 75 and centrally thereof for alignment with the groove 73 in the bracket base. Inasmuch as the vertical components of the bracket and pad assembly, including the tie wings, pad edges, tip of the pad and centrally arranged groove or scribe line, are parallel to each other, they all assist in lining up the bracket and pad assembly with the long axis of the clinical crown of the tooth. Additionally, all horizontal components of the assembly, including the archwire slot, gingival and occlusal tie wing edges, tip of the gingival pad edge 77 and the occlusal pad edge 76, are parallel with each other. They assist in lining up the assembly with the occlusal plane of the tooth. Therefore, the diagonal angulation built into the bracket and pad assembly shown in FIG. 6 avoids occlusal problems encountered with prior art bracket and pad assemblies and permit all components to line up with the brackets are properly bonded, as shown in FIG. 10. The present bracket having both diagonal torque and diagonal angulation allows the entire archwire slot to be centered over the base and which was not possible by heretofore known brackets.

The bracket 60 is secured to the pad by soldering and a layer of solder 79 is shown particularly in FIGS. 7 and 8. This provides a strong and secure bond between the back of the bracket and the pad. In order to assist in keeping the low compact profile of the bracket and to bring the archwire as close to the tooth as possible, the bracket base is cut out at its backside to a curvature to conform to the curvature on which it is to be mounted, and as seen particularly in FIG. 7, the backside 81 of the bracket has the same curvature as the front side 82 of the pad. The curvature extends along the mesiodistal length of the base portion of the bracket. Cutting off the backside of the bracket eliminates the need to splay the tie wings, thereby further enhancing the compactness of the bracket.

Because the center of the archwire slot in the bracket of the present invention is always over the center of the base, bracket slots on adjacent teeth will line up horizontally without varying bracket height, as illustrated in FIG. 9. This is not possible when torque is cut into the bracket face as in bracket A. Both bracket bases and faces line up with the invention, as seen in FIG. 9. Where torque is cut into the bracket face, the bonding positions of the bases must be varied, and such variable placement introduces unpredictable effects on torque and in-out control, and further, if the bases are lined up the slot height must vary. Variance in slot height will cause tipping or require second order wire bends. The built-in torque of the brackets of the present invention may be referred to as diagonal torque which improves torque control as well as control of tipping and in-out. As torque values change, the angles of the bracket sides change, but the gingival and occlusal sides and the facial and lingual sides remain parallel to each other. This further instigates the problem of occlusal interference encountered by prior known brackets.

Thus, the bracket of the invention eliminates the slot alignment and mass problems of prior art bracket A, and the tip projection problem of prior art bracket B. Further, the archwire slot is always over the center of the base for any angulation, but this is true with prior art brackets only when the angulation is zero. Bracket positioning is enhanced since the archwire slot can be lined up mesiodistally, thereby reducing the heretofore need to debond and rebond to correctly position the bracket on a tooth. This saves the orthodontist considerable time. Also, it looks better so aesthetics are satisfied, the patient's comfort is enhanced, and better results are obtained. The bracket of the invention, being smaller and narrower overall, defines a lower overall profile bringing the archwire slot, and therefore the archwire, closer to the tooth to define more direct action between tooth and wire.

It will be understood that modifications and variations may be effected without departing from the scope of the novel concepts of the present invention, but it is understood that this application is to be limited only by the scope of the appended claims.

The invention is hereby claimed as follows:

1. An orthodontic bracket for use with an archwire to impart corrective forces to a tooth comprising,
   a base portion having a backside for attachment to the tooth,
   a plurality of parallel tie wings integral with and extending from the base portion, said tie wings having parallel mesial and distal sides, outer labiobuccal faces extending substantially parallel to a plane common to the four corners of said base portion backside, gingival and occlusal tips with outer parallel gingival and occlusal edges, aligned labiobuccally opening archwire slots disposed centrally between the tips and having parallel opposed walls extending parallel to said occlusal and gingival edges, said labiobuccal faces forming an obtuse angle to one of the occlusal or gingival sides,
   whereby the buccolingual profile of the bracket defines a rhomboidal configuration and diagonal torque built into the bracket, one of said mesial or distal sides forming an obtuse angle with one of said gingival or occlusal sides thereby defining a rhomboidal labiobuccal profile for diagonal angulation.

2. The bracket defined in claim 1, wherein said base portion backside is formed to match the face of the tooth on which it is to be mounted.

3. The combination of an orthodontic bracket and a bonding pad adapted to be bondably attached to a tooth for use with an archwire to impart corrective forces to the tooth,
   said bracket having a pair of spaced tie wings extending from a base,
   said tie wings having parallel mesial and distal sides, outer labiobuccal faces extending parallel to a plane common to the four corners of said base portion backside, gingival and occlusal tips, aligned labiobuccally opening archwire slots disposed centrally between the tips and having parallel opposed walls extending parallel to said occlusal and gingival sides, and said labiobuccal faces forming an obtuse angle to one of the occlusal or gingival sides, whereby the buccolingual profile of the bracket defines a rhomboidal configuration and diagonal torque built into the bracket, and the labiobuccal profile being rhomboidal to define diagonal angulation,
   the labiobuccal face of the base between the tie wings having a groove extending centrally between and parallel to said tie wings,
   said bonding pad having parallel opposed side edges, a bottom edge forming an acute angle with one of said side edges, a top edge portion extending parallel to the bottom edge and disposed centrally between said tie wings, and a bracket engaging face with grooves aligning with the groove on the bracket base, the width of the pad being greater than the width of the bracket so that the side edges are spaced from the mesial and distal sides of the bracket, the side edges, bottom edge and top edge portion being parallel to the corresponding sides of the bracket such that the horizontal components of the bracket and pad enhance lineup with the incisal edge of a tooth and the vertical components enhance lineup with the long axis of the clinical crown.

4. The combination of claim 3, wherein said tie wings are parallel to each other.

5. The combination of claim 4, which further includes means bonding the bracket to the pad.

6. The combination of claim 5, wherein said bonding means includes a layer of solder between the bracket and pad.

7. The combination of claim 3, wherein the pad is arcuately formed to mate with the outer tooth surface, and the backside of the bracket is formed to mate with the pad.

8. The combination of claim 7, wherein the backside of the bracket is cut out to mate with the pad.

9. The combination of claim 3, wherein the top edge portion is centrally positioned between said tie wings and aligned with the top edges of the gingival tips.

10. An orthodontic bracket for use with an archwire to impart corrective forces to a tooth, said bracket comprising, a base portion having parallel gingival and occlusal sides, parallel mesial and distal sides, a tooth attaching surface at the lingual, and a pair of mesiodistally spaced tie wings at the buccolabial, each tie wing having a buccolabial face extending parallel to a plane extending through the edges of the tooth attaching surface, and gingival and occlusal tips, said tips having parallel opposed gingival and occlusal edges extending parallel to said gingival and occlusal sides, said buccolabial faces forming an obtuse angle with one of said gingival or occlusal sides such that the buccolingual profile of the bracket defines a rhomboidal configuration and builds a diagonal torque value into the bracket, one of said occlusal or gingival edges of said tips forming an obtuse angle with one of the mesial or distal sides such that the buccolabial profile of the bracket defines a rhomboidal configuration and builds a diagonal angulation into the bracket.

11. An orthodontic bracket for use with an archwire to impart corrective forces to a tooth, said bracket comprising, a base portion having a tooth engaging surface or backside for attachment to a tooth, a tie wing integral with and extending from said base portion, said tie wing having parallel gingival and occlusal sides, parallel mesial and distal sides, a buccolabial face extending parallel to a plane extending through the edges of the tooth engaging surface, a gingival tip and an occlusal tip, and a buccolabial opening and mesiodistally extending archwire slot disposed centrally between said tips, said tips having parallel opposed gingival and occlusal edges extending parallel to said gingival and occlusal sides, said slot having parallel opposed walls extending parallel to said gingival and occlusal sides and to said occlusal and gingival edges, said buccolabial face forming an obtuse angle with a line extended from one of said gingival or occlusal sides such that the buccolingual profile of the bracket defines a rhomboidal configuration and coacts with said slot to build a diagonal torque value into the bracket, wherein for all values of diagonal torque the gingival and occlusal sides remain parallel to each other, the parallel opposed walls of said slot remain parallel to said gingival and occlusal sides, and the buccolabial face and the tooth-engaging surface plane remain parallel to each other, and one of said occlusal or gingival edges forming an obtuse angle with a line extended from one of the mesial or distal sides such that the buccolabial profile of the bracket defines a rhomboidal configuration and coacts with said slot to build a diagonal angulation value into the bracket, wherein for all values of diagonal angulation the gingival and occlusal sides remain parallel to each other, the occlusal and gingival edges remain parallel to each other, and the parallel opposed walls of said slot remain parallel to the gingival and occlusal sides and the occlusal and gingival edges.

12. An orthodontic bracket for use with an archwire to impart corrective forces to a tooth, said bracket comprising, a base portion having a tooth engaging surface or backside for attachment to a tooth, a pair of identical spaced tie wings integral with and extending from said base portion, each tie wing having parallel gingival and occlusal sides, parallel mesial and distal sides, a buccolabial face extending parallel to a plane extending through the edges of the tooth engaging surface, a gingival tip and an occlusal tip, and a buccolabial opening and mesiodistally extending archwire slot disposed centrally between said tips, the mesial and distal sides of each tie wing being parallel to each other and the gingival and occlusal sides being respectively coplanar and the buccolabial faces being coplanar, said tips having parallel opposed gingival and occlusal edges extending parallel to said gingival and occlusal sides, said slots having parallel opposed walls extending parallel to said gingival and occlusal sides and to said occlusal and gingival edges, said buccolabial faces forming an obtuse angle with a line extended from one of said gingival or occlusal sides such that the buccolingual profile of the bracket defines a rhomboidal configuration and coacts with said slots to build a diagonal torque value into the bracket, wherein for all values of diagonal torque the gingival and occlusal sides remain parallel to each other, the parallel opposed walls of said slots remain parallel to said gingival and occlusal sides, and the buccolabial faces and the tooth-engaging surface plane remain parallel to each other, and one of said occlusal or gingival edges forming an obtuse angle with a line extended from one of the mesial or distal sides such that the buccolabial profile of the bracket defines a rhomboidal configuration and coacts with said slots to build a diagonal angulation value into the bracket, wherein for all values of diagonal angulation the gingival and occlusal sides remain parallel to each other, the occlusal and gingival edges remain parallel to each other, and the parallel opposed walls of said slots remain parallel to the gingival and occlusal sides and the occlusal and gingival edges.

* * * * *

UNITED STATES PATENT AND TRADEMARK OFFICE
CERTIFICATE OF CORRECTION

PATENT NO. : 4,659,309
DATED : April 21, 1987
INVENTOR(S) : Daniel A. Merkel

It is certified that error appears in the above-identified patent and that said Letters Patent are hereby corrected as shown below:

Col. 1, line 55, change "buccal" to —gingival—;
Col. 3, line 25, change "machinery" to —machining—;
    line 33, change "now" to —not—;
    line 50, delete "and distal" and insert —gingival and— before "occlusal";
Col. 4, line 6, change "a" to —an upper—;
    line 53, after "40" delete the comma (,); after "A" insert a comma (,);
    line 55, after "bracket" insert a comma (,); change "is" to —define—;
Col. 5, line 33, change "bracket" to —brackets—; delete ",";
    line 34, delete "distance" and insert —distance from opposing teeth— after "greater";
    line 59, change "labiobuccal" to —buccolingual—;
Col. 6, line 56, change "with" to —when—;
    line 23, change "oroder" to —order—;
Col. 7, line 28, change "instigates" to —eliminates—;
    line 59, after "sides," insert —parallel occlusal and gingival sides,—;
Col. 8, line 17, after "sides," insert —parallel occlusal and gingival sides,—;
Col. 9, line 29, change "buccolabial" to —buccolabially—;
Col. 10, line 18, change "buccolabial" to —buccolabially—;
Abstract, line 6, change "buccolingually" to —buccolabially—;

UNITED STATES PATENT AND TRADEMARK OFFICE
CERTIFICATE OF CORRECTION

PATENT NO. : 4,659,309

DATED : April 21, 1987

INVENTOR(S) : Daniel A. Merkel

It is certified that error appears in the above-identified patent and that said Letters Patent is hereby corrected as shown below:

Fig. 10, change numerals "65" to --60--.

Signed and Sealed this

First Day of September, 1987

Attest:

DONALD J. QUIGG

Attesting Officer

Commissioner of Patents and Trademarks

REEXAMINATION CERTIFICATE (2012th)
United States Patent [19]
Merkel et al.

[11] B1 4,659,309
[45] Certificate Issued May 18, 1993

[54] ORTHODONTIC BRACKET WITH RHOMBOIDAL PROFILE

[75] Inventor: Daniel A. Merkel; Lee H. Tuneberg, both of Sheboygan, Wis.

[73] Assignee: American Orthodontics Corporation, Sheboygan, Wis.

Reexamination Request:
No. 90/002,615, Dec. 23, 1991

Reexamination Certificate for:
Patent No.: 4,659,309
Issued: Apr. 21, 1987
Appl. No.: 784,794
Filed: Oct. 4, 1985

Related U.S. Application Data

[63] Continuation-in-part of Ser. No. 727,331, Apr. 25, 1985, abandoned.

Certificate of Correction issued Sep. 1, 1987.

[51] Int. Cl.⁵ .............................................. A61C 3/00
[52] U.S. Cl. ........................................ 433/9; 433/16
[58] Field of Search ............................... 433/8, 9, 16

[56] References Cited

U.S. PATENT DOCUMENTS

| | | | |
|---|---|---|---|
| D. 289,329 | 4/1987 | Evans | D24/16 |
| 2,778,110 | 1/1957 | Gooris | 433/167 |
| 3,391,461 | 7/1968 | Johnson | 433/17 |
| 3,477,128 | 11/1969 | Andrews | 433/16 |
| 3,660,900 | 6/1972 | Andrews | 433/16 |
| 4,068,379 | 1/1978 | Miller et al. | 433/9 |
| 4,369,033 | 1/1983 | Webb et al. | 433/9 |
| 4,415,330 | 11/1983 | Daisley et al. | 433/16 |

FOREIGN PATENT DOCUMENTS

2377188   9/1978   France .

OTHER PUBLICATIONS

"The Standard Straight-Wire" by A Company Inc., 11436 Sorren Valley Rd., San Diego, Calif. 92121, May 7, 1973.
The "A" Company Product Catalogue, 1981, pp. 54, 57–Cuspid Bracket (upper/lower).
The "A" Company Catalogue, 1981, p. 5.
The "A" Company Attract Bracket, 1986.
"The Refined Elegance of Diamonds", ORMCO Corp., 1983.
Ormco Catalog (1964) p. 13—Standard Edgewise Bracket.
"A" Company Product Catalog (1981) pp. 1, 7, 52–56.
Journal of Clinical Orthodontics, Jul., 1984, ad for The Attract Bracket.
Attract Bracket brochure, "A" Company, 1984.
"The Standard Straight-Wire Appliance", A Company, 1975 (7 pages).
Forestadent catalog, 1981 (2 pages).
Forestadent-Kompensations-Straight-Arch-Bracket, 1982 (2 pages).

*Primary Examiner*—John J. Wilson

[57] ABSTRACT

An orthodontic bracket for use with an archwire to impart corrective forces to a tooth, including a base portion attachable directly to a tooth, a bonding pad or a band and at least one tie wing extending from the base portion which includes gingival and occlusal tips and an archwire slot opening buccolingually and extending mesiodistally. The buccolingual profile of the bracket is rhomboidal, wherein the backside of the base portion and the front face are parallel and the occlusal and gingival sides are parallel, while an obtuse angle is defined between the outer face of the bracket and one of the occlusal or gingival sides depending upon the tooth on which the bracket is mounted and the torque desired.

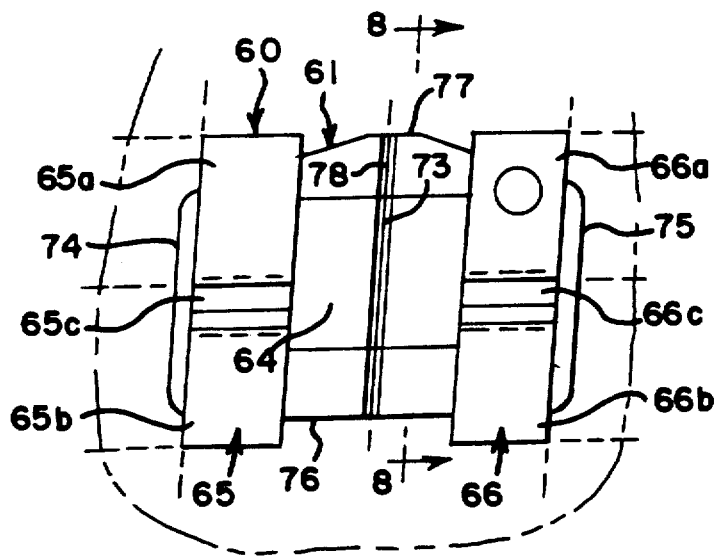

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 1–10 and 12 is confirmed.

Claim 11 having been finally determined to be unpatentable, is cancelled.

* * * * *